(12) United States Patent
Fritzler et al.

(10) Patent No.: US 9,149,242 B2
(45) Date of Patent: Oct. 6, 2015

(54) MULTI-SOURCE CT SYSTEM

(75) Inventors: Sven Fritzler, Breuberg-Sandbach (DE); Jan Matschulla, Oderwitz (DE)

(73) Assignee: Siemens Aktiengesellschaft, Munich (DE)

( * ) Notice: Subject to any disclaimer, the term of this patent is extended or adjusted under 35 U.S.C. 154(b) by 642 days.

(21) Appl. No.: 13/499,419

(22) PCT Filed: Sep. 28, 2010

(86) PCT No.: PCT/EP2010/064365
§ 371 (c)(1),
(2), (4) Date: Jul. 12, 2012

(87) PCT Pub. No.: WO2011/039189
PCT Pub. Date: Apr. 7, 2011

(65) Prior Publication Data
US 2012/0269317 A1    Oct. 25, 2012

(30) Foreign Application Priority Data

Sep. 30, 2009    (DE) .......................... 10 2009 043 221

(51) Int. Cl.
*A61B 6/03*    (2006.01)
*A61B 6/00*    (2006.01)
*H05G 1/70*    (2006.01)

(52) U.S. Cl.
CPC .................. *A61B 6/504* (2013.01); *A61B 6/032* (2013.01); *A61B 6/405* (2013.01); *A61B 6/4007* (2013.01); *A61B 6/4014* (2013.01); *A61B 6/482* (2013.01); *A61B 6/507* (2013.01); *H05G 1/70* (2013.01)

(58) Field of Classification Search
CPC ..... A61B 6/4014; A61B 6/4007; A61B 6/482
USPC ........................................ 378/9, 92, 124, 134
See application file for complete search history.

(56) References Cited

U.S. PATENT DOCUMENTS

| 4,607,380 | A | * | 8/1986 | Oliver ........................... 378/138 |
| 5,010,563 | A | * | 4/1991 | Laurent et al. ................ 378/132 |
| 6,888,919 | B2 | | 5/2005 | Graf |
| 7,453,976 | B1 | * | 11/2008 | Yin ................................... 378/9 |
| 2005/0265521 | A1 | * | 12/2005 | Deuringer et al. ............ 378/138 |
| 2006/0193430 | A1 | | 8/2006 | Kuhn |
| 2006/0285633 | A1 | | 12/2006 | Sukovic et al. |
| 2008/0260093 | A1 | | 10/2008 | Bontus |
| 2010/0020935 | A1 | | 1/2010 | Dafni |
| 2010/0135557 | A1 | | 6/2010 | Krauss et al. |

FOREIGN PATENT DOCUMENTS

DE    103 46 682 A1    5/2005

* cited by examiner

*Primary Examiner* — Phillip A Johnston
*Assistant Examiner* — Kevin Chung
(74) *Attorney, Agent, or Firm* — Schiff Hardin LLP

(57) ABSTRACT

A multi-source computed tomography system has a first x-ray source and a second x-ray source that are respectively optimized for different imaging procedures and can be used simultaneously in the multi-source CT system. The first x-ray source can be optimized for higher power short-term operation and the second x-ray source can be optimized for lower power, longer term operation.

5 Claims, 2 Drawing Sheets

MULTI-SOURCE CT SYSTEM

BACKGROUND OF THE INVENTION

1. Field of the Invention

The invention relates to a multi-source CT system for the generation of X-ray images of an object under examination of the type having at least one first and one second X-ray radiation source mounted in a rotatable manner about a rotational axis, each emitting a radiation beam and at least one X-ray radiation detector that is struck by the radiation beams.

2. Description of the Prior Art

A significant future requirement of computer tomography (CT) scanners is ever greater rotational frequencies of gantries. A faster rotation of the gantry around the patient shortens the recording (data acquisition) time, which in turn results in higher temporal resolution of the recordings. This is of great importance in cardiology in particular, as here a high temporal resolution at the beating heart also influences spatial resolution and thus the possibility of detecting arteriosclerosis at an early stage. In the case of higher rotational frequencies, however, the mAs requirement must also be met in order to reach a certain image quality. Ever greater radiation power must be delivered, so that these X-ray tubes must be specially designed for the requisite short-term load of typically 1 s.

An increase in the rotational frequency, however, also increases the strain on the components of the gantry as a result of greater centrifugal force, so that the rotational frequency is currently limited to 3 to 4 Hz. In order nonetheless to increase the number of projections achieved per unit of time, the use of dual- or multi-tube CT systems is known, in which two or more X-ray emitter-detector units are arranged, offset at an angle in a gantry housing. Furthermore, a known method for better differentiation of a variety of tissue types is to scan the area under investigation simultaneously with X-ray radiation of different spectral distribution, that is to say with different maximum X-ray energy or a different spectral centroid.

A dual-source CT system for examination of a patient is known from DE 10 2007 024 158 A1, having a gantry housing, in which two X-ray tubes are arranged offset an at angle with oppositely arranged detector systems, which rotate about a system axis for scanning of the patient, while the patient is conveyed along the system axis through the measuring area of the CT system by means of the controllable patient couch. During a dual-energy CT examination, the two similar X-ray tubes are operated with different acceleration voltages, so that the two X-ray spectra used differ greatly and also deliver different absorption values in the assigned detectors upon irradiation of the patient.

In addition to short-duration scans with a maximum of a few seconds duration, CT systems are also used for whole-body scans and perfusion measurements. In such cases the X-ray emitter must be designed for recording times of up to one minute. The X-ray emitter that has been designed so as to be able to be used in short-term scans is subjected to extreme stresses in such longer term operation, which in particular impacts its useful life.

SUMMARY OF THE INVENTION

An object of the present invention is to optimize a multi-source CT system in relation to the requirements for different types of recording.

The basic idea of the invention consists, in the case of a multi-source CT system with at least two X-ray radiation sources, of providing different X-ray radiation sources, which differ significantly in particular with respect to their technical structure and the maximum X-ray radiation power achievable for a particular recording duration. At least one of the X-ray radiation sources is optimized for a first mode of operation and at least one second X-ray radiation source for a second mode of operation of the CT system. In particular the inventive CT system preferably comprises just one technically highly complex X-ray radiation source, which can generate an extremely high X-ray radiation power for a short recording duration. The second X-ray radiation source, on the other hand, is designed for continuous output. The second X-ray radiation source is preferably used exclusively for whole-body or perfusion measurements.

By means of the invention it is possible, in the case of a multi-source CT system with a multiplicity of X-ray radiation sources, to optimize the latter in each case for their special purpose. This results in a reduction in costs for the multi-source CT system concerned. As the X-ray radiation sources used are at least predominantly only operated in the mode of operation for which they have been optimized, their useful life is also prolonged thereby.

According to the invention the first and second X-ray radiation sources differ by a factor at least in respect of the maximum X-ray radiation power that they can generate for a particular recording duration. This factor preferably lies in the range 1.3 to 3.

In a preferred embodiment of the invention, the first X-ray radiation source has a magnetic bearing for the anode plate. Rotational frequencies of the rotating anode of up to 1000 Hz are thereby enabled. Furthermore, the first X-ray radiation source advantageously has a steel plate thermally coupled with the anode plate for heat dissipation purposes. The first X-ray radiation source is here designed and optimized for recording times of less than 5 s.

The second X-ray radiation source of the inventive multi-source CT system is of simpler construction compared with the first X-ray source. In particular this here involves a rotary X-ray source designed for permanent output over durations of far more than 40 s, with a rotating anode mounted by means of a ball or plain bearing.

DESCRIPTION OF THE PREFERRED EMBODIMENTS

Figure 1:
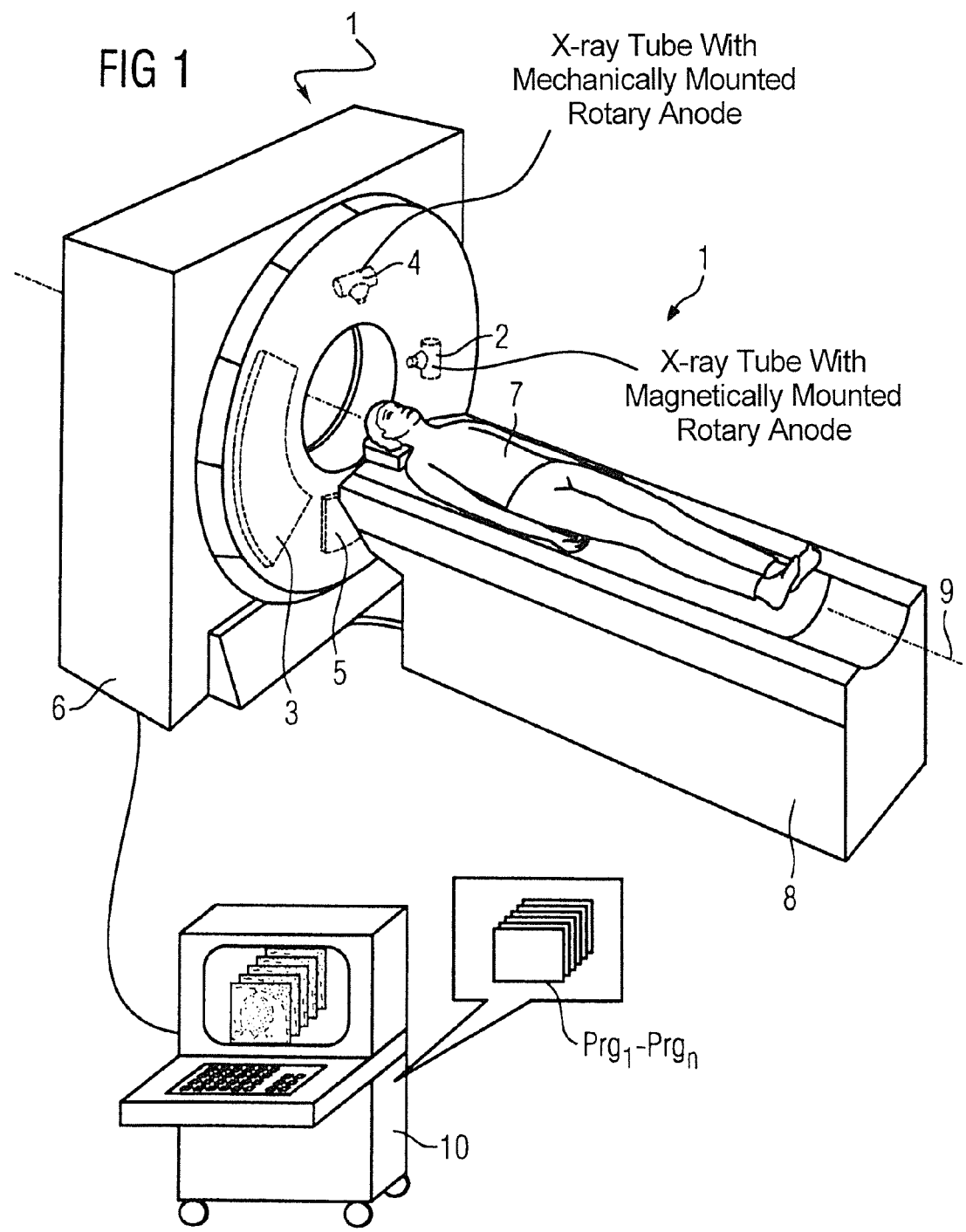
FIG. 1 shows an inventive multi-source CT system.

One example of a dual-source CT system 1 according to the invention is shown in FIG. 1. This CT system 1 has a gantry housing 6, in which are two X-ray tubes 2 and 4 arranged offset at an angle, with oppositely located detector systems 3 and 5, which rotate about a system axis 9 for the scanning of the patient 7, while the patient 7 is conveyed by means of the controllable patient couch along the system axis 9 through the measuring area of the CT system. A control and arithmetic unit 10 which contains computer programs $Prg_1$-$Prg_n$ in its memory that perform the control and reconstruction during operation serves to handle control, reconstruction and execution of the inventive method.

Dual-energy operation is possible in the case of the CT system 1 for better differentiation of various tissue types in the area of examination of the patient 7. To this end, the X-ray absorption must be measured at least in relation to two different energy spectra. This takes place with the aid of the dual-energy CT scanner 1, which permits the reconstruction of two independent images for at least one axial section through the patient 7, which were generated with different effective X-ray spectra. A simultaneous scan with two different tube voltages preferably takes place. It is important for image generation to determine the different absorption effect on the two different X-ray radiation powers.

In the example shown here the two X-ray tubes 2 and 4 are operated with different acceleration voltages, so that the two X-ray spectra used differ greatly and also deliver different absorption values in the assigned detectors upon irradiation of the patient 7.

According to the invention the two X-ray tubes 2 and 4 differ in their technical aspects. The X-ray tube 2 is capable of emitting a considerably higher X-ray radiation power for a short recording time in the range up to 5 s than the X-ray tube 4. In dual-energy operation, the X-ray tube 2 is thus operated with the higher acceleration voltage. In contrast to this the X-ray tube 4 is designed for a recording time of 40 s and more. However X-ray radiation power as high as with X-ray tube 2 cannot be achieved in this case, even for a short period. For dual-energy scans the X-ray tube 4 is thus operated with the lower acceleration voltage compared with X-ray tube 2. It is further used—preferably with the X-ray tube 2 switched off—for whole-body scans and perfusion measurements which require recording times of 10 s or more.

The X-ray tube 2 takes the form of a technically complex X-ray tube, in which the anode plate is mounted by a magnetic bearing and which is also actuated via a magnetic field. For heat dissipation purposes the anode plate is thermally coupled to a radiation surface. The rotational frequency of the anode plate can further amount to 1000 Hz. By means of this construction of the X-ray tube 2, an extremely high X-ray radiation power can be achieved for a short time, such as a radiation power of at least 100 kW for a duration of at least 2 seconds.

By contrast to this, the X-ray tube 4 takes the form of a simply constructed rotary piston tube. Although in this case the maximum achievable X-ray radiation power is significantly lower than with the X-ray tube 2 (for example only 50% compared with the X-ray tube 2, such as a radiation power of at least 60 kW for a duration of at least 30 seconds), a relatively high X-ray radiation power can still be achieved for recording times of 1 min and more.

Figure 2:
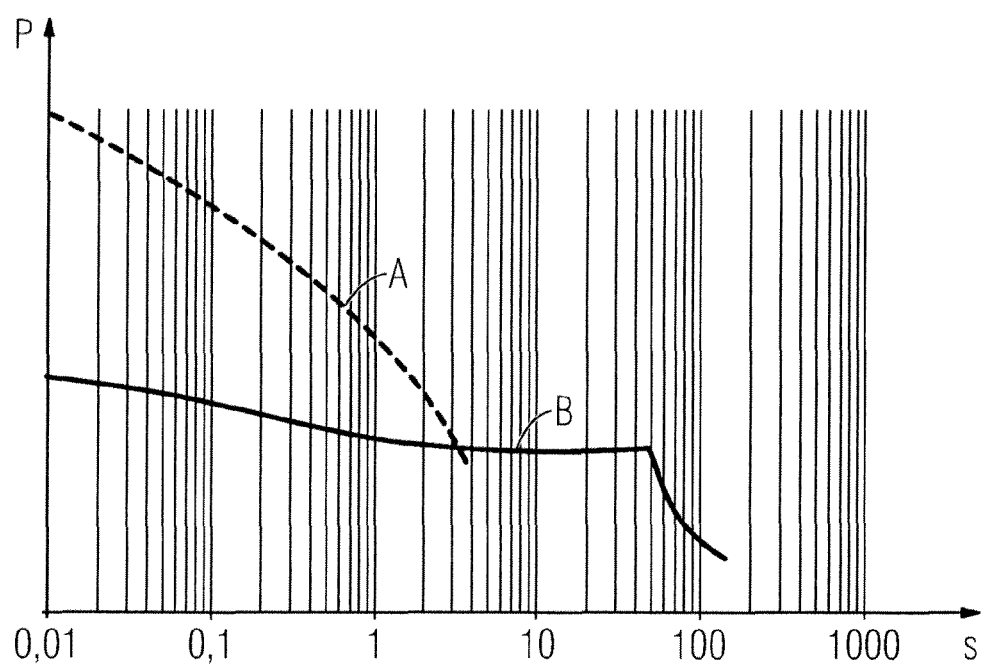
FIG. 2 shows the X-ray radiation power dependent upon the operational duration for different X-ray radiation sources.

The diagram according to FIG. 2 illustrates the relationship between the maximum X-ray radiation power P depending on the recording time s.

The critical load curve A of the X-ray tube 2 shows a markedly higher X-ray radiation power in the short-term range of up to one second. By contrast, the X-ray tube 4—illustrated by the critical load curve B—enables a long permanent output of up to 40 s, which lies significantly above the permanent output of X-ray tube 2.

Through the use of two technically different X-ray tubes 2 and 4 the inventive dual-source CT system is optimized both for short- and long-term recordings. Dual-energy operation is additionally also possible. As compared with conventional CT systems, the two X-ray tubes 2 and 4 need not be operated at the respective limit for the different types of recording which are thereby possible, the useful life of the X-ray tubes 2 and 4 is significantly increased, and the failure rate reduced.

In a particular embodiment the "Dual Energy" principle can be attained in such a way that the X-ray tube 2 is operated at a high tube voltage, as less tube current is here required for the same photon flux. The X-ray tube 4 on the other hand is operated with a lower tube voltage and higher current.

Although modifications and changes may be suggested by those skilled in the art, it is the intention of the inventors to embody within the patent warranted heron all changes and modifications as reasonably and properly come within the scope of their contribution to the art.

We claim as our invention:

1. A multi-source computed tomography system, comprising:
    a first x-ray source comprising a magnetically mounted rotating anode from which a first x-ray beam is emitted;
    a first radiation detector situated to detect x-rays in said first x-ray beam emitted by said first x-ray source;
    a control computer configured to operate said first x-ray source and said first radiation detector in a first mode to acquire first tomographic data from a subject situated between said first x-ray source and said first radiation detector;
    a second x-ray source comprising a mechanically mounted rotating anode, said second x-ray source emitting a second x-ray beam;
    a second radiation detector situated to detect x-rays in said second x-ray beam emitted by said second x-ray source;
    said control computer being configured to operate said second x-ray source and said second radiation detector in a second mode to acquire second tomographic data from the subject, which is also situated between said second x-ray source and said second radiation detector;
    each of said first x-ray source and said second x-ray source being mounted so as to rotate around a same rotational axis that proceeds through said subject; and
    said control computer being configured to operate said first x-ray source in said first mode to emit x-ray radiation at a first x-ray radiation power for a first duration, and to operate said second x-ray source in said second mode with a second radiation power for a second duration, with said first x-ray radiation power being higher than said second x-ray radiation power and said first duration being less than said second duration.

2. A multi-source computed tomography system as claimed in claim 1 wherein said control computer is configured to operate said first x-ray source in said first mode with said first x-ray radiation power being higher by a factor greater than 1.3 than said second x-ray radiation power of sais second x-ray source in said second mode.

3. A multi-source computed tomography system as claimed in claim 1 wherein said control computer is configured to operate said first x-ray source to emit x-rays in said first mode with said first x-ray radiation power of at least 100 kW for said first duration of at least two seconds.

4. A multi-source computed tomography system as claimed in claim 1 wherein said control computer is configured to operate said second x-ray source to emit x-rays in said second mode with said second x-ray radiation power of at least 60 kW for said second duration of at least 30 seconds.

5. A multi-source computed tomography system as claimed in claim 1 wherein said control computer is configured to operate said first x-ray source to emit x-rays in said first mode with said first x-ray radiation power of at least 100 kW for said first duration of at least two seconds, and to operate said second x-ray source to emit x-rays in said second mode with said second x-ray radiation power of at least 60 kW for said second duration of at least 30 seconds.

\* \* \* \* \*